United States Patent
Fabian et al.

(10) Patent No.: US 7,784,468 B2
(45) Date of Patent: *Aug. 31, 2010

(54) SURGICAL IMPLEMENT DETECTION SYSTEM

(76) Inventors: Carl E. Fabian, 577 NE. 96th St., Miami Shores, FL (US) 33138; Philip M. Anderson, III, 37 Winding Way, Madison, NJ (US) 07940

( * ) Notice: Subject to any disclaimer, the term of this patent is extended or adjusted under 35 U.S.C. 154(b) by 2000 days.

This patent is subject to a terminal disclaimer.

(21) Appl. No.: 10/265,555

(22) Filed: Oct. 8, 2002

(65) Prior Publication Data

US 2003/0066537 A1    Apr. 10, 2003

Related U.S. Application Data

(60) Provisional application No. 60/328,357, filed on Oct. 10, 2001.

(51) Int. Cl.
*A61B 19/00* (2006.01)
(52) U.S. Cl. .................... 128/899; 600/424; 340/572.1; 340/572.2; 340/572.4; 340/551
(58) Field of Classification Search .............. 340/572.1, 340/572.2, 551, 572.4; 128/899; 600/424
See application file for complete search history.

(56) References Cited

U.S. PATENT DOCUMENTS

| | | | |
|---|---|---|---|
| 2,740,405 A | 4/1956 | Riordan | 128/296 |
| 3,422,816 A | 1/1969 | Robinson et al. | 128/296 |
| 3,587,583 A | 6/1971 | Greenberg | 128/296 |
| 4,114,601 A | 9/1978 | Abels | 600/20 |
| 5,057,095 A | 10/1991 | Fabian | 604/362 |
| 5,105,829 A | 4/1992 | Fabian et al. | 128/899 |
| 5,107,862 A | 4/1992 | Fabian et al. | 128/899 |
| 5,188,126 A | 2/1993 | Fabian et al. | 128/899 |
| 5,190,059 A | 3/1993 | Fabian et al. | 128/899 |
| 5,329,944 A | 7/1994 | Fabian et al. | 128/899 |
| 5,629,498 A * | 5/1997 | Pollock et al. | 177/15 |
| 5,664,582 A * | 9/1997 | Szymaitis | 128/898 |
| 5,923,001 A * | 7/1999 | Morris et al. | 177/245 |
| 5,936,527 A * | 8/1999 | Isaacman et al. | 340/572.1 |
| 6,026,818 A | 2/2000 | Blair | 128/899 |
| 6,366,206 B1 * | 4/2002 | Ishikawa et al. | 340/573.1 |

* cited by examiner

*Primary Examiner*—Brian Casler
*Assistant Examiner*—James Kish
(74) *Attorney, Agent, or Firm*—Ernest D. Buff & Associates LLC; Ernest D. Buff (57) ABSTRACT

Surgical implements used during an operating procedure are detected in human tissue. Markers attached to the surgical implements change their impedance at a preselected frequency in the presence of an electromagnetic field. Each of the markers is thereby provided with signal-identifying characteristics. The signal-identifying characteristics are detected outside the operating room in an accurate, reliable manner. Potential interference with operating room electronic instrumentation is avoided, the possibility of operator error is reduced and system cost and space requirements are substantially lowered.

11 Claims, 9 Drawing Sheets

SURGICAL IMPLEMENT DETECTION SYSTEM

This application claims the benefit of U.S. Provisional Application No. 60/328,357, filed Oct. 10, 2001.

BACKGROUND OF THE INVENTION

1. Field of the Invention

The present invention relates to a system for detection of surgical implements; and more particularly, to a method and means for detecting a marked surgical implement such as a sponge, scissors, clamp, or other instrument within a surgical wound in human or animal tissue, irrespective of its position or orientation therewithin.

2. Description of the Prior Art

During the course of a surgical operation it is common practice for articles, such as surgical sponges, gauzes, instruments and the like, to be placed into a wound cavity. Notwithstanding rigorous precautions and attendant surgical procedures, such items are sometimes inadvertently lost during surgery and remain within the patient. When this happens, the patient can suffer serious consequences, including unexplained mass, pain, infection, tissue erosion, fistulization, intestinal obstruction, and possibly death. The problem of retained surgical implements has existed since the earliest days of surgery and persists to this day. Procedures conventionally employed to prevent post-surgical implement retention include a manual search of the wound by the surgeon prior to closure and a careful accounting for all materials inserted and removed from the wound. The accounting function is customarily carried out by the operating room staff, usually the circulating nurse. Despite these precautionary measures the accidental retention of surgical implements continues to occur with disturbing regularity, estimated to be as often as once per thousand operations, even in prestigious institutions, and is regarded by surgeons as a major unsolved problem.

At present, physical count combined with manual search remain the primary methods used in detection of retained surgical implements. Most surgical instruments are composed of metal, and are easily detectable by x-ray. Sponges are customarily tagged with radiopaque markers to make them also visible on x-ray, but intraoperative x-rays are not routinely performed before completion of the operation owing to several disadvantages, including inconvenience, expense, loss of operative time, and radiation exposure. Postoperative x-rays are subject to some of the same disadvantages and are not generally done unless there is a question of a retained implement. Moreover, even when postoperative x-rays are taken; retained surgical implements are not infrequently overlooked.

To overcome the difficulty of detecting retained surgical implements, it has been suggested that the implements be provided with a radioactive tracer. This technique, disclosed by U.S. Pat. No. 2,740,405 to Riordan, is subject to obvious hazards associated with use, storage and disposal of radioactive materials.

It has also been proposed that surgical sponges be marked with a flexible plastic impregnated with either paramagnetic or ferromagnetic materials in the form of powders. Detection of these marked sponges is accomplished by a metal detector. This method, taught by U.S. Pat. No. 3,422,816 to Robinson et al., provides very small signals difficult to detect over the width of a patient's body. In addition, the Robinson et al. technique provides no discrimination against other metal objects, such as screws, prostheses, and other metallic objects which, though present within the surgical wound, may be intentionally appointed for retention therewithin.

Yet another proposal, advanced by U.S. Pat. No. 3,587,583 to Greenberg, involves use of surgical sponges marked with magnetized particles whose presence is detectable with magnetodiodes. In practice, however, the magnetic field generated by these particles is too small to be readily detected by the diodes.

U.S. Pat. No. 4,114,601 to Ables discloses the use of a small transponder fixed to a surgical sponge or instrument. This transponder exhibits gyromagnetic resonance at preselected frequencies. Detection is accomplished by nonlinear mixing of two frequencies impinging upon the transponder. The gyromagnetic resonance effect disclosed by Ables is a high frequency phenomenon, existing at frequencies of the order of about 5 gigahertz (5,000,000,000 cycles/sec). These frequencies, known as microwaves, are absorbed readily by tissue. In use of the Ables type transponder, the energy developed goes primarily into heating tissue, rather than exciting the transponder into gyromagnetic resonance, making it undesirable.

U.S. Pat. No. 6,026,818 to Blair et al. discloses a method and device for the detection of unwanted objections in surgical sites, including a medically inert detection tag affixed to objects such as medical sponges or other items used in body cavities during surgery. The tag is said preferably to have a resonance with low Q. A preferred detection system employs a hand-held detection wand used within approximately 12 to 18 inches of the surgical site.

U.S. Pat. Nos. 5,057,095, 5,107,862, 5,190,059, 5,329,944, 5,105,829, and 5,188,126 to Fabian et al. disclose the use of various technologies to detect surgical implements marked with a tag and left within the surgical wound after completion of surgery and prior to closing the wound. In these patents, the detection apparatus is utilized in the operating room, since detection is accomplished before closure of the wound. While these systems are effective in detecting marked surgical implements, their use within the operating room may be restricted by certain considerations. For example, the electromagnetic fields generated during operation of previous detection systems may interfere with other essential medical electronics, such as heart and brain wave monitors, extant in the operating room. The latter systems are frequently vulnerable to ambient fields that may degrade their sensitivity and the quality of the data they produce, which in some cases is crucial to the patient's well-being. Moreover, other operating room equipment that itself generates electromagnetic fields may have to be deactivated during operation of a surgical implement detection system, lest the interfering signals overload the implement detection system's input or otherwise compromise its sensitivity. As a result, there remains a need for systems that are not constrained by exigencies specific to the operating room environment.

Furthermore, existing devices require operating room personnel to diligently scan each patient for marked items, so the potential for operator error is always present. Moreover, to assure proper detection of surgical implements during an operation, a separate unit must be dedicated to each operating room, causing cost and space requirements to be high. Given the intensity of the operating room environment, the inherent risks for the patient, and the need for intense and sustained concentration by the attending medical personnel, systems which can minimize the need for the personnel to carry out logistical functions such as accounting for instruments are highly sought.

Thus, up to the present time, the optimal means for detecting post-operatively retained surgical implements, though addressed by numerous workers in the art, have yet to be found. Instead, the detection systems heretofore proposed each have features for which improvement has long been sought.

SUMMARY OF THE INVENTION

The present invention provides a system and method for detecting surgical implements within human tissue in an accurate, reliable manner. Potential electrical interference with operating room instrumentation is avoided, and system cost and space requirements are significantly reduced.

Generally stated, the invention provides an improved system for detecting in human tissue a surgical implement used during a procedure carried out in an operating room. A marker attached to the surgical implement changes its impedance at a preselected frequency in the presence of an electromagnetic interrogating field. The change of impedance provides the marker with at least one signal-identifying characteristic. In accordance with the improvement, the surgical implement with its attached marker is deployed within the wound during the operation and if said surgical implement and attached marker are inadvertently retained within the wound, the signal-identifying characteristics are detected outside the operating room but before leaving the operating room suite, thus allowing timely removal In one aspect, the invention provides a system wherein an interrogating means generates an electromagnetic field having a preselected frequency, preferably modulated as a series of pulses, the marker attached to the surgical implement preferably resonates at a preselected frequency in response to the field, and a detecting means detects a ring-down signal of the marker between the pulses.

The marker preferably comprises a magnetomechanical element having a mechanical resonance frequency substantially equal to the preselected frequency, and a biasing means for magnetically biasing the magnetomechanical element. A housing is provided for enclosing the magnetomechanical element and the bias means, wherein the magnetomechanical element is free to mechanically vibrate.

Alternatively, the marker is comprised of an electrically resonant LRC circuit, or as a further alternative, the marker is comprised of a mechanically resonant piezoelectric material and coils.

Further, the invention provides a method for detecting an accidentally-retained surgical implement by attaching a marker to a surgical implement appointed for use during an operating procedure, placing a surgical implement detector outside of an operating room and shielding the area around the surgical implement detector. The patient is subjected to an interrogating field generated by said surgical implement detector after the surgery. Detection of the marker is indicated visually and/or audibly by the detector.

The positioning of the detector of the present system outside the operating room affords both important technical and logistical advantages. As noted above, in the operating room there can be significant limitations on the allowable emission of radiated electromagnetic fields to prevent disruption of the functioning of essential equipment. Locating the detection equipment of the invention away from the immediate operating room: (i) removes certain operational limits that would otherwise constrain the emission of such fields and (ii) prevents electromagnetic fields generated by other operating room equipment from interfering with the present detection system. Situating the equipment in a more favorable location, e.g., at some distance from the operating room, allows various measures to be taken to optimize detection accuracy, which may include optimal detection geometry, redundancy of detection equipment, shielding, stronger signal strength, etc. In addition, a system positioned so that every patient must unavoidably pass through an active interrogation zone during post-operative egress to the recovery room ensures that a thorough scanning procedure is routinely accomplished without the need for specific action by the attending operating room personnel. Also, depending on the layout of the operating suite, there are a limited number of exits; often there is only one. Accordingly, one, or at most a small number of systems, e.g., located in a commonly shared exit passageway, are sufficient to service a plurality of operating rooms, assuring full coverage of patients treated in any of the operating rooms, instead of needing a dedicated system in each.

Advantageously, the method and apparatus of the invention detect retention of surgical implements with far greater accuracy than methods and means involving a physical count of implements that enter and exit the wound. The apparatus is inexpensive to construct, safer for the patient than postoperative X-rays and avoids risk to the environment posed by radioactive tracers. Generation of a strong signal is effected in a highly reliable manner. The signal is more easily distinguished than signals generated by known magnetic detection systems and is generated without the heating of tissue caused by microwave detection systems. Detection of marked implements is accomplished irrespective of marker position or orientation within the wound. Possible electrical interference with operating room instrumentation is minimized and space requirements and system costs are substantially reduced. Detection of retained surgical implements is accomplished with greater ease and speed, at less expense and more reliably than with systems in which the interrogating field is applied by operating room personnel during the operating procedure.

BRIEF DESCRIPTION OF THE DRAWINGS

The invention will be more fully understood and further advantages will become apparent when reference is had to the following detailed description of the preferred embodiment of the invention and the accompanying drawings, in which.

DESCRIPTION OF THE PREFERRED EMBODIMENTS

Figure 1:
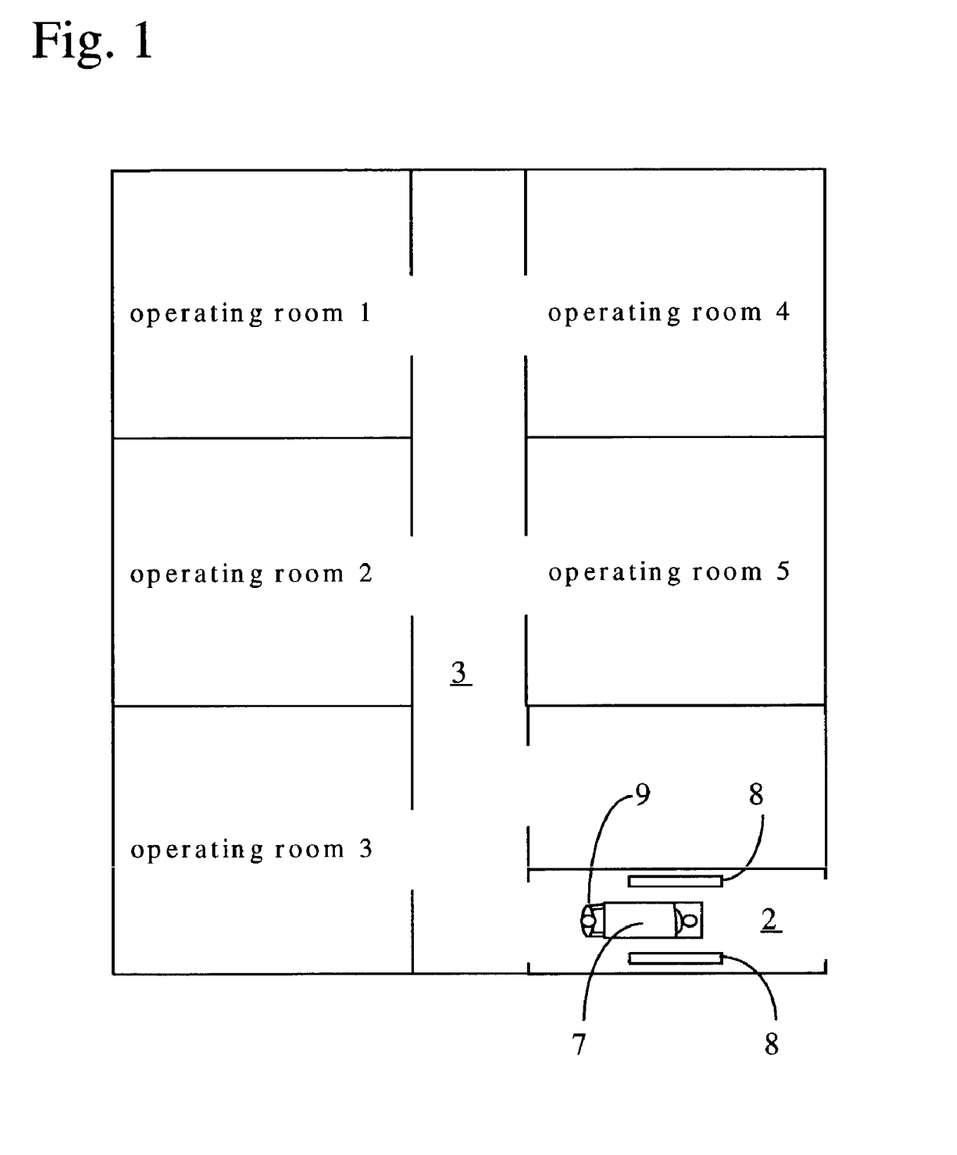
FIG. 1 is a schematic representation depicting an overhead view of a typical operating room complex in a hospital incorporating the present invention.
Figure 2:
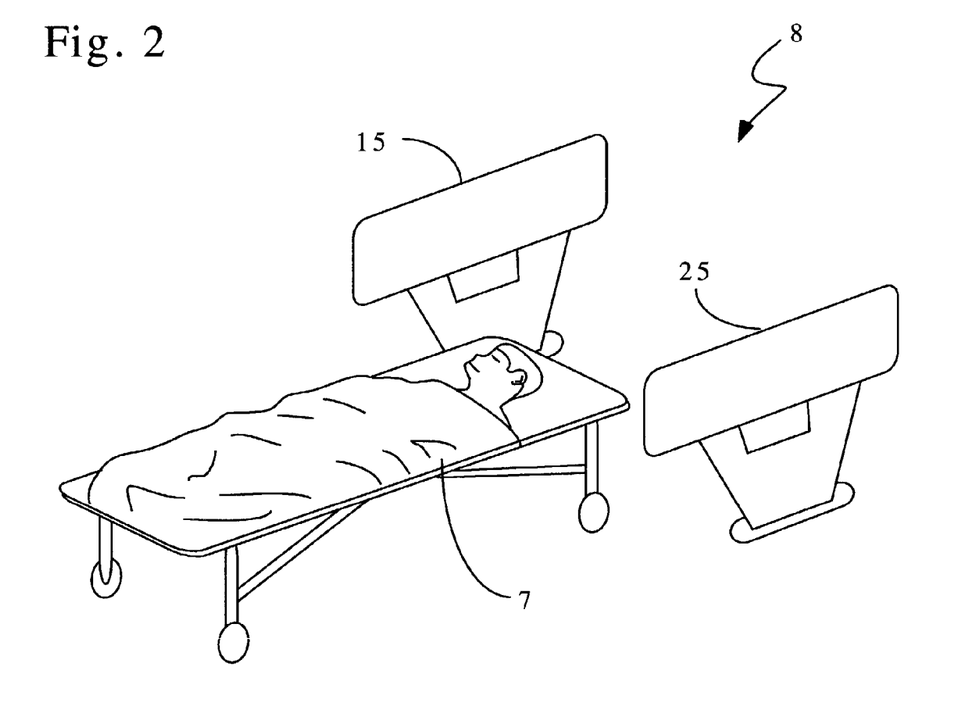
FIG. 2 is a perspective view depicting a post-operative patient on a gurney entering a surgical implement detector.

Referring to the drawings, there is shown in FIG. 1 a system for detection of surgical implements. An overhead view of a typical operating room complex in a hospital is depicted. Entrance hall 2 leads into a common hall 3 servicing five operating rooms. Entrance hall or passageway 2 is provided with a surgical implement detector 8. A post-operative patient on a gurney 7 is pushed by an attendant 9 through a detector 8. FIG. 2 is a perspective view depicting a post-operative patient on a gurney 7 entering a detector 8. Detector 8 is comprised of an interrogating means 15 and a receiving means 25.

Figure 3:
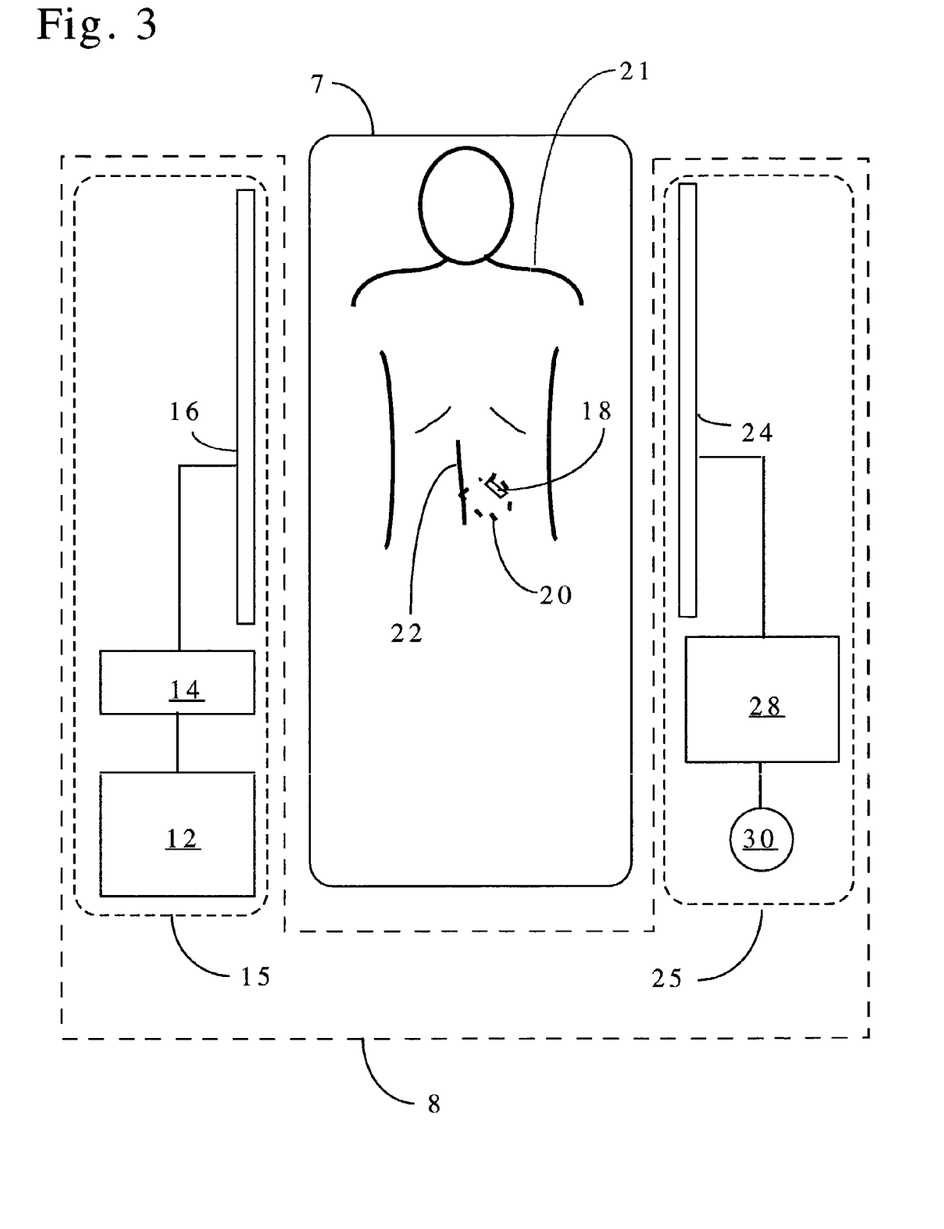
FIG. 3 is a block diagram depicting the surgical implement detector and gurney with patient.

Referring to FIG. 3, a marker 18 is secured to a surgical implement, such as a sponge 20, positioned within a surgical wound 22 within patient 21. Marker 18 is characterized by resonance at a preselected resonance frequency. It is driven by the interrogating field produced by detector 8 into resonance at the preselected frequency, by detector 8, causing marker 18 to undergo a large change in impedance. This impedance change at the resonance frequency provides marker 18 with a signal-identifying characteristic. By signal-identifying characteristic is meant at least one characteristic that is detectable by remote electronic means and that provides, by its presence or absence, affirmative indication of the presence or absence of the marker associated therewith. A signal-identifying characteristic may be uniquely associated with each individual marker. Alternatively, some or all markers of a given class of markers may share a substantially identical identifying characteristic. Detector 8 generates an electromagnetic field comprising at least the preselected resonance frequency, thereby driving marker 18 into resonance. Preferably, the preselected frequency is below 1 gigahertz to avoid the absorption of the field by tissue that would undesirably compromise the detection capability of the system.

Referring further to FIG. 3, there is shown an interrogating means 15 comprised of frequency-generating means 12, field-changing means 14, and field-generating means 16. Frequency-generating means 12 generates a frequency encompassing the resonant frequency of marker 18 and supplies the power signal to energize the field-generating means 16. Either a single frequency waveform may be generated or the frequency may be chirped, that is, swept within a preselected range of frequencies encompassing the frequency of interest. Field-generating means 16 comprises at least one, and preferably a plurality of antenna elements. Below 10 MHz, the antenna elements are preferably comprised of one or more coils. Above 10 MHz, the antenna elements are preferably comprised of one or more monopole antennas or, alternatively, dipole antennas. When energized, field-generating means 16 produces the requisite electromagnetic interrogating field. The antenna elements may be driven individually or collectively. The field emanating from plural coils or antennas is generally a superposition of the fields produced by each of the individual coils or antennas. The dimensions of the coils and marker and the distances between the coils and the marker are generally much less than the wavelength of electromagnetic radiation at the frequencies generally used for magnetomechanical systems (e.g., about 50 kHz). Consequently, the field produced by each current-carrying coil in such a system may be predicted generally using known principles, e.g. the Biot-Savart Law.

Field-changing means 14 varies the amplitude and direction of the interrogating field to alter the electromagnetic dipole coupling between the field and marker 18. In one aspect of the invention, field-changing means 14 comprises a mechanical drive that changes at least one of the position and orientation of the one or more antenna elements of field-generating means 16. Such a mechanical drive may be assembled using a combination of known electrical, pneumatic, or mechanical components, structures, and drive systems to rotate or translate the antenna elements.

Figure 9:
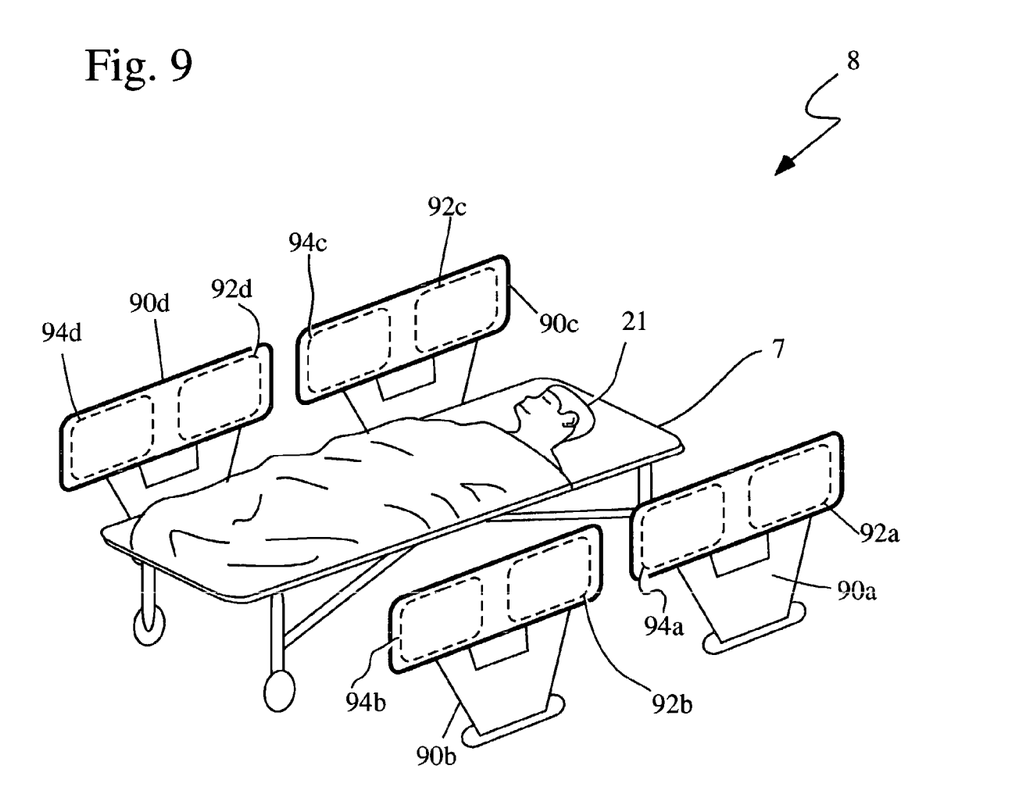
FIG. 9 is a perspective view of a post-operative patient on a gurney within an interrogation zone of a surgical implement detection system comprising a plurality of antennas and receiver elements.

More preferably, field-changing means 14 comprises an electrical, electromechanical, or semi-conductor-based switching system that permits one or more antenna elements to be selectively energized. It is further preferred that plural elements are coupled, preferably in series, to provide an interrogating field having higher intensity and wider spatial coverage than possible with a single element. The relative polarity of the connection to each antenna is pre-selected for each combination of elements that are to be collectively excited. One such implementation is depicted by FIG. 9 and comprises four substantially identical field-generating coils, 92a, 92b, 92c, and 92d disposed, respectively, in floor-mounted pedestals 90a, 90b, 90c, and 90d. Each of the coils is connected to a semiconductor switching system or multiplexer (not shown) configured to selectively connect in series any two coils chosen from coils 92a, 92b, 92c, and 92d to the frequency-generating means (not shown). It will be understood that the requisite electronics, including the switching system and the frequency-generating means, may be located either in the pedestals or at a remote location. In addition, other implementations may employ a different number of coil antenna elements, and the elements may be located with their axes either at a common height, as depicted by FIG. 9, or at different heights. The elements may also be wall, floor, or ceiling mounted.

The polarity of a series connection of antenna elements established by the switching system may also be inverted, thereby changing by a half cycle the relative phase of the time-varying field produced by each coil. Each combination of a pair of coils and a relative polarity gives rise to an interrogating field within the interrogation zone that has a different spatial distribution and vectorial orientation. A marker generally is found to be most sensitive to excitation by an interrogating field having a strong vector component along a particular preferred marker orientation. As a result, sequential excitation of the target by differently oriented interrogating fields markedly increases the probability that a given marker will be favorably oriented within at least one of such field patterns, thus markedly decreasing the probability that a marker will pass through the interrogation zone without being activated by the interrogating field and consequently detected. In a system having but a single fixed antenna element, there is a slight probability that a marker in an orientation that is fortuitously unfavorable might escape detection.

Receiving means 25 depicted by FIG. 3 comprises detecting means 28, detecting antenna 24, and indicating means 30. Detecting means 28, having detecting antenna 24, detects the change in impedance as either phase change or ring-down at the preselected resonant frequency. Detecting antenna 24 comprises at least one, and preferably a plurality of receiver elements. Below 10 MHz, the receiver elements are is preferably comprised of one or more coils. Above 10 MHz, the receiver elements are preferably comprised of one or more monopole antennas or, alternatively, dipole antennas. It will be understood by those skilled in the art that some implementations of the present invention will employ the same antenna elements for both field generation and receiving functions. The indication means comprises a source of distinctive sound or light to alert relevant personnel to the detection of a retained surgical item requiring follow-up medical intervention and care. Preferably, indicating means 30 is a flashing light. Alternatively indicating means 30 is a buzzer. As a further alternative, indication means 30 comprises a combination light and sound source. The indication means may also further provide a printed record or a message transmitted to a computer system memorializing the detection of a marker.

The same considerations of magnetic superposition and reciprocity that make preferable the use of a field-generating means comprising a plurality of antenna elements also apply to the detecting antenna of the present system, which preferably comprises a plurality of receiver elements. In addition, it is likewise preferable that receiving means 25 comprise an electrical, electromechanical, or semi-conductor-based receiving switching system by which one or more receiver elements are selectively connected to detecting means 28. The strength of the signal received from the dipolar field emanating from the marker is enhanced by proximity of the marker to the receiver elements and favorable relative orientation of the marker and the one or more active receiver elements. It is further preferred that plural receiver elements be coupled to enhance the sensitivity and coverage of the detector. Like the interrogating field, the oscillating electromagnetic field produced by the marker during its ring-down period has a spatial distribution and vectorial orientation. Connecting the output of the antenna system in sequentially varied different configurations to the detection system enhances the sensitivity of the system to signals and the probability of detection. One such receiving means employing a plurality of coils is illustrated in FIG. 9. In addition to field-generating antenna elements, pedestals 90a, 90b, 90c, and 90d further comprise receiver elements, coils 94a, 94b, 94c, and 94d. Each of the coils is coupled to a receiving switching system (not shown) which selectively couples one or more of the coils to the detecting means (not shown).

The combination of varying the orientation of the detector and interrogation field is especially beneficial in detecting markers that produce a weak output. Enhanced detection sensitivity advantageously allows use of markers having reduced amounts of magnetic material and reduced size that otherwise could not reliably be detected.

There are three types of marker resonance particularly useful in the system of the present invention: (1) magnetomechanical—in which case energy is alternatively stored in mechanical vibration and magnetic field, such as can be seen with a magnetostrictive amorphous metal ribbon; (2) electromechanical—in which case energy is alternately stored in mechanical vibration and electric field, such as can be seen with a piezoelectric crystal; and (3) electromagnetic—in which case energy is alternately stored in an inductor and a capacitor, such as can be seen with an LRC circuit. When excited by interrogating means 15, markers of each of these types will generate a dipole field that exhibits a characteristic phase difference with the exciting field near resonance and a shift in phase as the exciting field's frequency traverses resonance. Since energy from the exciting field is being stored in these resonant elements, removal of this field will result in the gradual, dissipative loss of the energy from the resonant system, yielding a dipole field having a characteristic "ring-down" of energy. That is to say, the dipole field is oscillatory, but has an amplitude that diminishes with time, generally within an exponentially decaying envelope. This ring-down provides a signal-identifying characteristic to a resonant marker, allowing the dipole field it emits after excitation to be distinguished from other ambient electromagnetic fields, which do not exhibit a ring-down in synchrony with activation by the interrogating field.

Figure 4:
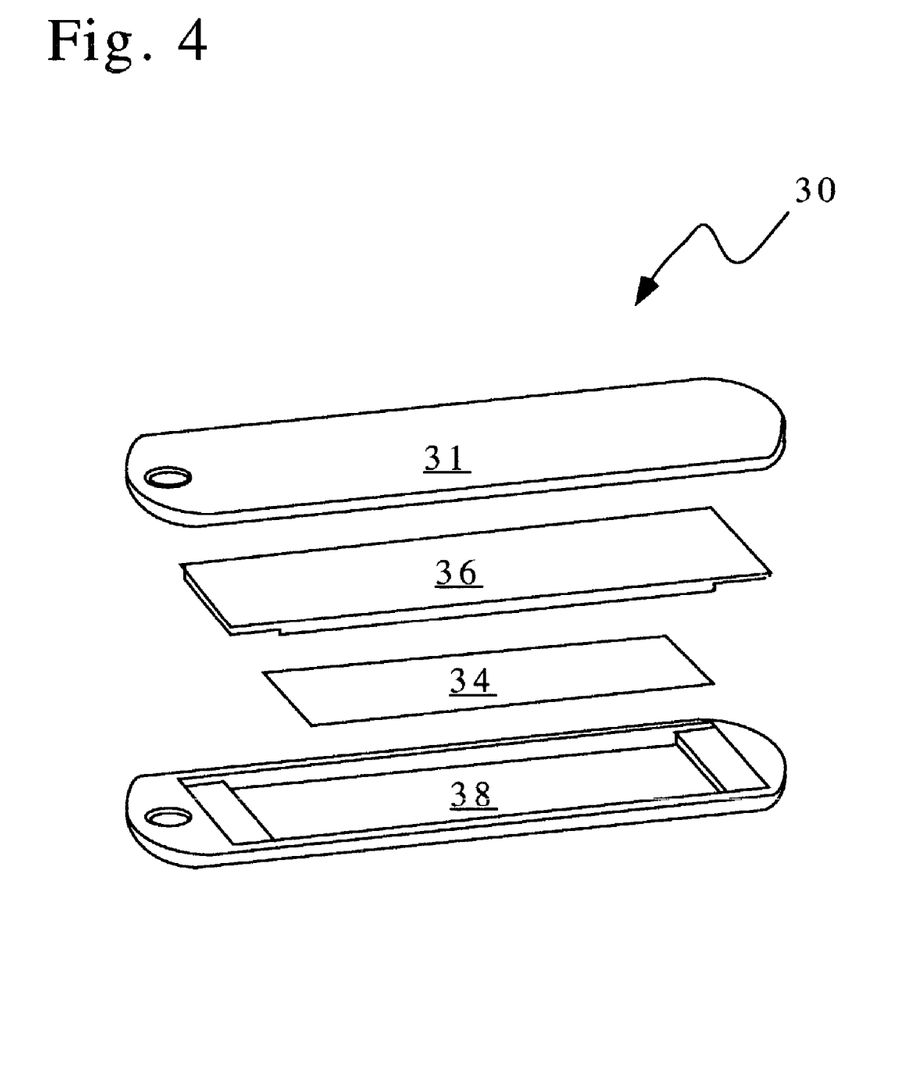
FIG. 4 is an exploded view illustrating a magnetomechanical marker.

FIG. 4 is an exploded view of a preferred embodiment of the marker. Magnetomechanical marker 30 comprises at least one strip of magnetostrictive material 34 adapted to be magnetically biased and thereby armed to resonate mechanically at a preselected frequency within the frequency band of the interrogation field. A ferromagnetic element 36 disposed adjacent to the strip 34 of magnetostrictive material is adapted, upon being magnetized, to serve as a bias means to arm the strip 34 to resonate at the preselected frequency. Preferably element 36 is composed of a hard or semi-hard magnetic material, i.e., a material having a magnetic coercive field (or coercivity) sufficiently high to resist demagnetization in any magnetic field it may be expected to encounter inadvertently. Case 38 and lid 31 comprise a material, such as ABS plastic, that will remain inert within the wound throughout the surgery. The strip 34 of magnetostrictive material has a magnetomechanical-coupling factor greater than zero. The ferromagnetic element 36 is preferably a molded composite composed of a hard ferromagnetic powder, such as barium ferrite, and a plastic such as nylon or delrin, and preferably may comprise at least a portion of case 38 or lid 31. The concentration of magnetic powder to plastic is selected to supply a field substantially equal to the magnetic field required to obtain optimum magnetomechanical coupling in the magnetostrictive strip 34. For example, approximately 3 Oersteds of magnetic bias is required to obtain maximum magnetomechanical coupling in an unannealed amorphous alloy whose composition is substantially equal to 40% Fe, 38% Ni, 4% Mo, and 18% B, percentages in atomic weight percent. In one aspect of the invention, one or more of the magnetic materials may comprise a sufficient density of heavy atoms to render the marker radiopaque. For example, barium-containing compounds such as barium ferrite are known to possess significant radiodensity. As such, the marker may also be detected by known x-ray techniques if additional confirmation of its presence within a patient is desired. Alternatively, ferromagnetic element 36 is a thin strip of metal alloy such a vicalloy or Arnochrome. Upon exposure to the dc magnetic field, generated by the ferromagnet 36, or by an external bias means such as a dc electromagnet, the marker is characterized by a substantial change in its effective impedance as it undergoes resonance when the preselected frequency is supplied by the interrogating field. When the interrogating field is removed, the magnetostrictive strip 34 exhibits the characteristic ring-down at the resonant frequency. The preselected frequency is chosen to be substantially equal to the mechanical resonant frequency of the magnetostrictive strip or a harmonic thereof.

Figure 5:
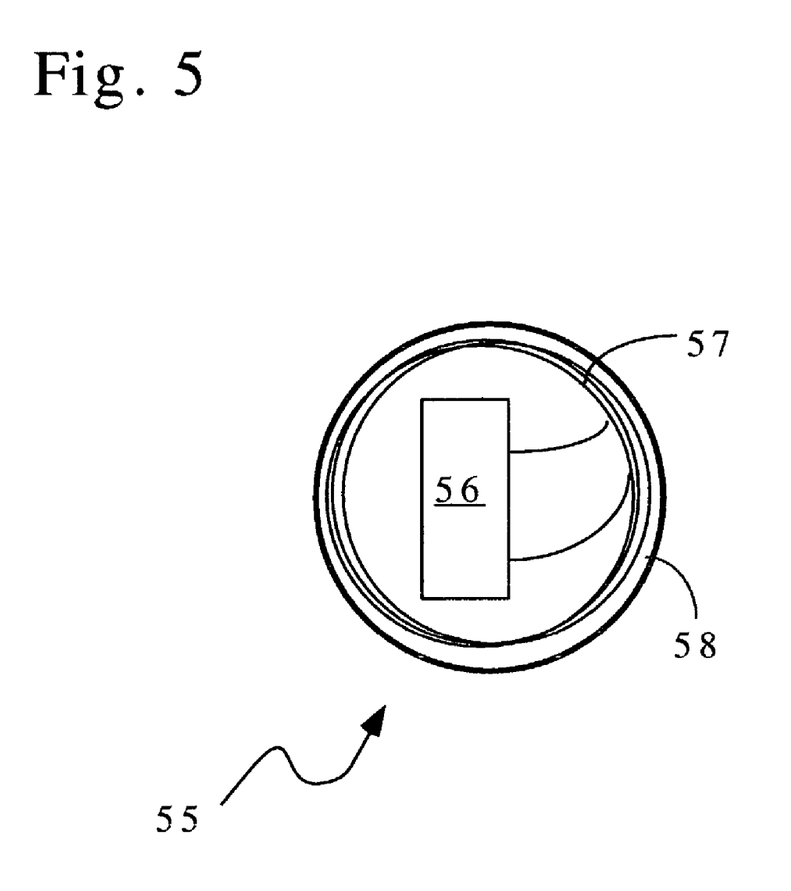
FIG. 5 is a perspective view illustrating the main elements of an electromechanical marker.

An alternative embodiment of the marker is shown in FIG. 5. In the embodiment shown, the marker 55 comprises a piezoelectric element 56. The piezoelectric element comprises a piezoelectric material, such as a quartz crystal, PZT, or a piezoelectric film, such as Kynar film. The piezoelectric element is provided with terminals for electrically connecting the element to other circuit elements such as a coil. An air-core coil 57, occupying the inside diameter of case 58, is terminated across piezoelectric element 56 and is inductively coupled to the exciting field of the detector 8. Alternatively, an iron or ferrite core inductor is used in place of the coil 57. The marker 55 is characterized by a substantial change in its effective impedance at the resonant frequency which provides the marker with signal identity. When the field is removed, the marker exhibits ring-down at the resonant frequency. The preselected frequency is chosen to be substantially equal to the mechanical resonant frequency of the piezoelectric material or a harmonic thereof.

Figure 6:
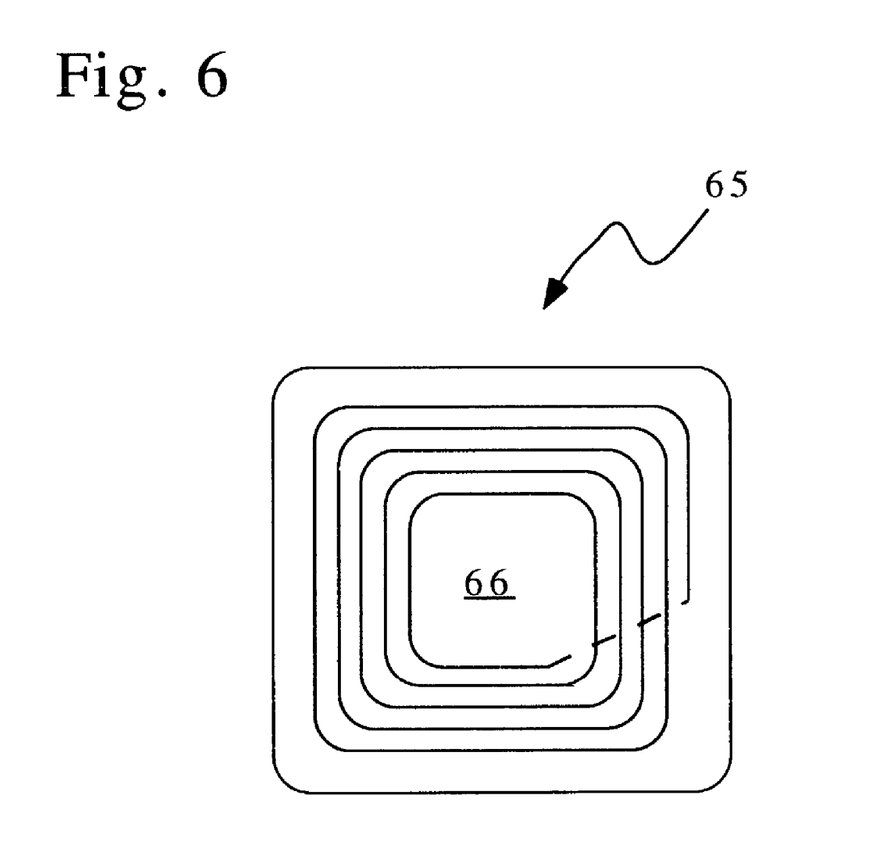
FIG. 6 is a plan view depicting the main elements of an electromagnetic marker.

A further embodiment of the marker is shown in FIG. 6. In that embodiment, marker 65 comprises a printed circuit coil 66. The resonance frequency of coil 66 is determined by the inductance, capacitance and resistance of the coil. Alternatively, marker 65 comprises an inductor, resistor, and capacitor in a series or parallel LRC circuit. Such a marker is rendered small with the use of surface mounted components. In either case, the marker is excited by inductive coupling between the exciting field of the detector 8 and the inductance of the marker circuit elements and the marker is characterized by a substantial change in its effective impedance at the resonant frequency, thus providing marker 65 with a signal-identifying characteristic. This signal identity is characterized by phase change and electrical ring-down at the resonant frequency when the applied field is removed. The preselected frequency is chosen to be substantially equal to the electrical resonant frequency of the LRC circuit or a harmonic thereof.

Figure 7:
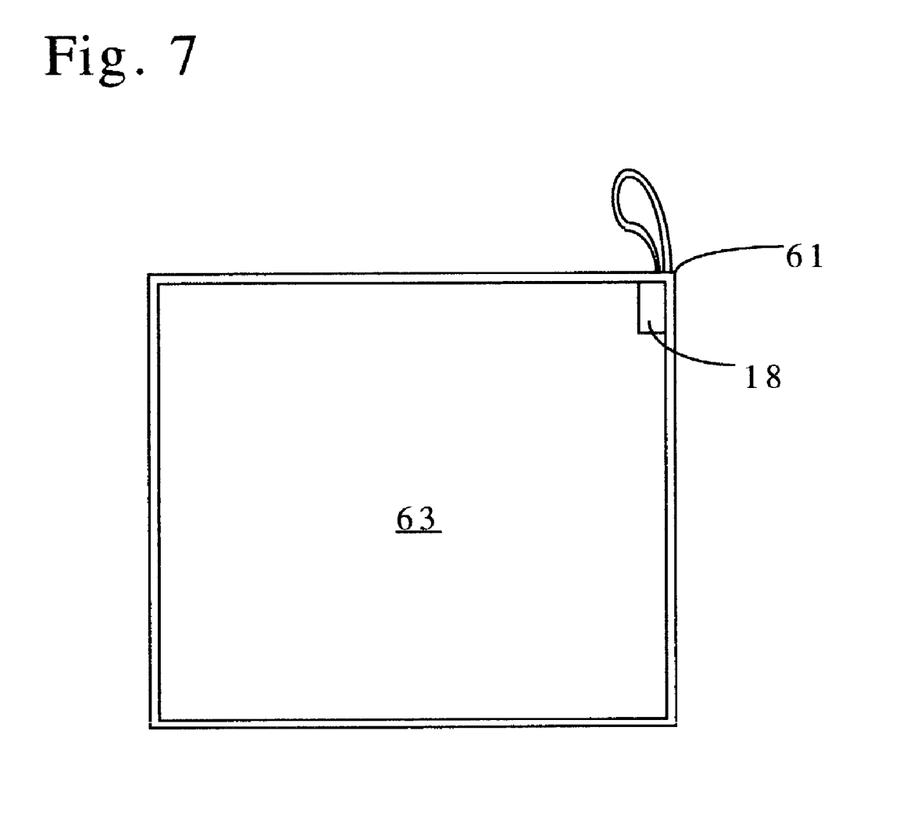
FIG. 7 is a frontal view depicting a surgical sponge with a marker sewn into a corner.
Figure 8:
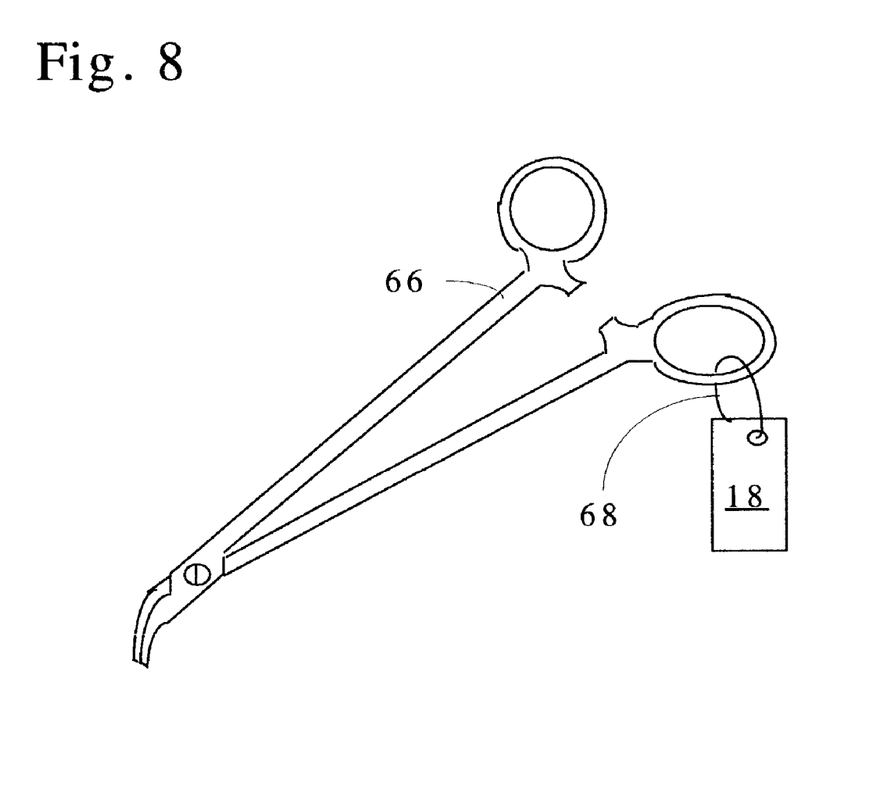
FIG. 8 is a perspective view depicting a surgical forceps having a marker attached thereto by a lanyard.

The marker can be attached to various surgical implements. As shown in FIG. 7, marker 18 is sewn into a corner 61 of a surgical sponge 63. FIG. 8 shows marker 18 attached to forceps 66 by lanyard 68. Alternatively, marker is fixed to forceps 66 by adhesive. It will further be understood that while the present invention is herein described in connection with the surgical treatment of human patients, the system and method may also be used in the treatment of animals.

In an alternative embodiment of the invention, the marker comprises a soft magnetic material which radiates an electromagnetic field having a significant content of harmonics of the frequency of the interrogating field. The harmonic content of such a marker provides signal identity, since other, more massive ferrous objects radiate a dipole field with comparatively little or no harmonic content in response to the interrogating field. Such a marker preferably comprises an elongated strip of amorphous magnetic material. Representative materials suitable for use in a marker in this implementation are disclosed in U.S. Pat. No. RE35,402.

In one aspect of the invention, detector 8 is placed outside the operating room, preferably along an exit route therefrom. This permits engineering of the detection site to optimize detection parameters such as detection geometry, redundancy of equipment, shielding, optimal signal strength and minimal cross-interference with other ambient electromagnetic signals. Furthermore, with such a common location, only one detector is needed per operating room complex, minimizing cost and floor space. To detect surgical implements inadvertently left in the body after surgery, a marker is attached to each surgical implement appointed for use within the surgical wound. A surgical-implement detector is positioned outside of an operating room. After surgery, the patient is subjected to the interrogation field generated by the surgical-implement detector, which provides a visual and/or audible signal if the marker is present.

More specifically, to detect a surgical implement inadvertently left in a surgical wound of a patient, a marker is attached to each surgical implement appointed for use during an operating procedure. A surgical-implement detector is positioned outside of the operating room. The marker comprises a marker element adapted to undergo resonance at a preselected frequency generated by the surgical-implement detector. The detector further comprises detection circuitry capable of detecting the signal-identifying characteristic of any marker present within the interrogation zone. Following the surgical procedure, the patient is moved through an interrogation zone in which an electromagnetic interrogating field generated by the surgical-implement detector is present. If a surgical instrument bearing a marker has been inadvertently left within the patient, the associated signal-identifying characteristic will be activated during passage through by the interrogation zone. Upon detection of this characteristic by the detector, a visual or audible alarm connected thereto is triggered, alerting relevant personnel to the need for further medical intervention.

In one implementation, a system of the invention is used to protect an operating-room suite comprising a plurality of operating rooms which share a common exit hall. The field-generating means comprises at least one antenna element and the detecting antenna comprises at least one receiver element, both elements being disposed adjacent the wall of the exit hall. Preferably, the elements are permanently attached to the wall. The system may also employ floor or ceiling mounted antenna or receiver elements. Preferably the elements are located approximately at the height of a patient being conveyed on a conventional surgical gurney for maximal sensitivity. It is also preferred that the system comprise plural antenna and receiver elements, and switching means of one of the aforesaid types to connect the elements and sequentially provide a plurality of interrogating field patterns and detector sensitivity directions. Being removed from the operating room environment, the present system may be operated continuously without fear of compromising vital medical electronic equipment frequently used in each operating room, yet be active continually for detecting the presence of retained implements in surgical patients being transported from the operating room suite via the hall, e.g. enroute to a recovery room or similar facility. Instead of being operated continuously, the system of the invention may also be operated intermittently, being activated by a floor-mounted pressure pad, a motion detector, the interruption of a light beam traversing the hall through which a surgical gurney bearing a patient must pass, or other similar device.

Preferably, to further reduce possible interference with operating room instrumentation, the walls of the room or hall containing the surgical-implement detector are lined with shielding. When the preselected frequency is below 10 MHz, the shielding is preferably comprised of a high permeability magnetic material, low coercive field material, such as permalloy, mumetal, or other the like. Above 10 MHz, the walls are preferably lined with a grounded metal screen. Optionally, the floors and ceiling of the area around the surgical implement detector are also shielded. The shielding may serve a dual function: (i) to prevent the interrogating field and other interfering noise radiated from the detector when in operation from deleteriously entering equipment used in a nearby operating room or other related area, and (ii) to reduce the level of electromagnetic noise coming from operating room equipment that might otherwise overload the surgical-implement detector's input or reduce its sensitivity to actual marker signals.

Having thus described the invention in rather full detail, it will be understood that such detail need not be strictly adhered to but that various changes and modifications may suggest themselves to one skilled in the art, all falling within the scope of the invention as defined by the subjoined claims.

What is claimed is:

1. In a system for detecting in human or animal tissue a surgical implement used during an operating procedure carried out in an operating room, said system comprising a surgical implement detector and a marker attached to said surgical implement that changes its impedance at a preselected interrogating frequency in the presence of an electromagnetic interrogating field, whereby said marker is provided with a signal-identifying characteristic, the improvement wherein:

said surgical implement detector is placed outside of the operating room and comprises an interrogating means, a detecting means, and an indication means;

said interrogating means is configured to generate said electromagnetic interrogating field, said field having said preselected interrogating frequency modulated as a series of pulses;

said marker resonates at a preselected resonant frequency and radiates a marker dipole field in response to said interrogating field;

said signal-identifying characteristic is a ring-down of said dipole field;

said detecting means is configured to detect said ring-down between said pulses; and said indication means is configured to be activated by said detecting means in response to the detection of said marker;

said interrogating means comprises a frequency-generating means, a field-generating means, and a field-changing means, said frequency-generating means generating said preselected interrogating frequency, said field-generating means receiving said preselected interrogating frequency and generating within an interrogation zone said electromagnetic interrogating field, and said field-changing means varying at least one of the amplitude and direction of said electromagnetic interrogating field to alter the electromagnetic dipole coupling between said marker element and said interrogating field, and said interrogation zone is located outside said operating room;

wherein said surgical implement detector is configured to detect when said signal-identifying characteristic is found within said wound and said interrogation zone.

2. A system as recited by claim 1, wherein said marker comprises:
 a. at least one magnetomechanical element having a mechanical resonant frequency substantially equal to said preselected interrogating frequency;
 b. a bias means for magnetically biasing said magnetomechanical element; and
 c. a housing enclosing said magnetomechanical element and said bias means, wherein said magnetomechanical element is free to mechanically vibrate.

3. A system as recited by claim 1, wherein said field-generating means comprises at least one antenna element and said field-changing means comprises means for moving said at least one antenna element to change at least one of the position and orientation thereof.

4. A system as recited by claim 3, wherein said detecting antenna comprises at least one selectively activatable receiver element and said antenna-changing means comprises means for moving said at least one receiver element to change at least one of the position and orientation thereof.

5. A system as recited by claim 1, wherein said detecting means comprises a detecting antenna, an antenna-changing means, and a detector circuit connected to said detecting antenna, said detecting antenna receiving said marker dipole field, said antenna-changing means varying at least one of the orientation and position of said detecting antenna relative to said marker element to alter the electromagnetic dipole coupling therebetween, and said detector circuit detecting the presence of said ringdown and activating said indication means in response thereto.

6. A method for detecting a surgical implement left within a patient after surgery carried out on the patient in an operating room, the method comprising the steps of:
 a. attaching a marker to said surgical implement before use during said surgery, said marker having a signal-identifying characteristic in the presence of an electromagnetic interrogating field;
 b. placing a surgical-implement detector outside of an operating room, said detector being adapted to generate said electromagnetic interrogating field outside said operating room and detect said signal-identifying characteristic;
 c. removing said patient from said operating room after said surgery and thereafter subjecting said patient to said electromagnetic interrogating field generated by said surgical-implement detector;
 d. detecting said signal-identifying characteristic; and
 e. activating an indication means in response to the detection of said signal-identifying characteristic indicative of the presence of said implement.

7. A method for detecting a surgical implement as recited by claim 6, further comprising the step of:
 a. shielding an area surrounding said surgical-implement detector.

8. A method for detecting a surgical implement as recited by claim 6, wherein said marker comprises at least one marker element adapted to undergo resonance at a preselected frequency generated by said surgical-implement detector.

9. A method for detecting a surgical implement as recited by claim 8, wherein said marker element is magnetomechanically resonant.

10. A method for detecting a surgical implement as recited by claim 6, wherein said detector is disposed along an exit from said operating room.

11. A method for detecting a surgical implement as recited by claim 10, wherein said detector is disposed along an exit servicing a plurality of operating rooms.

\* \* \* \* \*